United States Patent
Inglese et al.

(10) Patent No.: US 9,486,141 B2
(45) Date of Patent: Nov. 8, 2016

(54) IDENTIFICATION OF DENTAL CARIES IN LIVE VIDEO IMAGES

(75) Inventors: Jean-Marc Inglese, Bussy-Saint Georges (FR); Wei Wang, Minhang (CN); Liwei Song, Pudong (CN); Victor C. Wong, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 367 days.

(21) Appl. No.: 13/205,715

(22) Filed: Aug. 9, 2011

(65) Prior Publication Data
US 2013/0038710 A1 Feb. 14, 2013

(51) Int. Cl.
*A61B 5/00* (2006.01)
*G06T 3/00* (2006.01)
*G06T 7/00* (2006.01)

(52) U.S. Cl.
CPC .......... *A61B 5/0071* (2013.01); *A61B 5/0088* (2013.01); *A61B 5/4547* (2013.01); *G06T 3/0075* (2013.01); *G06T 7/0024* (2013.01); *G06T 2207/10064* (2013.01); *G06T 2207/30036* (2013.01)

(58) Field of Classification Search
CPC .................................................... A61B 5/0071
USPC ........................ 382/128, 154; 348/50, 66, 77
See application file for complete search history.

(56) References Cited

U.S. PATENT DOCUMENTS

| | | | |
|---|---|---|---|
| 6,438,275 B1 | 8/2002 | Martins et al. | |
| 7,668,355 B2 | 2/2010 | Wong et al. | |
| 7,702,139 B2 | 4/2010 | Liang et al. | |
| 2006/0239526 A1 | 10/2006 | Jonusauskas et al. | |
| 2008/0056551 A1 | 3/2008 | Wong et al. | |
| 2008/0170764 A1* | 7/2008 | Burns | A61B 5/0088 382/128 |
| 2008/0310712 A1* | 12/2008 | Edgar | H04N 1/62 382/167 |
| 2009/0185712 A1* | 7/2009 | Wong | A61B 5/0088 382/100 |
| 2009/0232355 A1* | 9/2009 | Minear | G06K 9/00201 382/103 |
| 2010/0165089 A1* | 7/2010 | Liang et al. | 348/66 |
| 2010/0309300 A1* | 12/2010 | Chhibber | A61B 5/0059 348/77 |

(Continued)

FOREIGN PATENT DOCUMENTS

| | | |
|---|---|---|
| EP | 2 083 389 | 7/2009 |
| WO | WO2008/088672 | 7/2008 |
| WO | WO 2010/083623 A1 | 7/2010 |

OTHER PUBLICATIONS

International Search Report mailed Jan. 30, 2013 for International Application No. PCT/US2012/047269, 2 pages.

(Continued)

*Primary Examiner* — Tung Vo
*Assistant Examiner* — Rowina Cattungal

(57) ABSTRACT

A method for identification of caries, executed at least in part on data processing hardware, captures a plurality of blocks of digital tooth images, each block of tooth images comprising a fluorescence image and one or more reflectance images. At least one registered fluorescence image is generated from the fluorescence image and the one or more reflectance images. A combined image is generated using each of the one or more reflectance images and the at least one registered fluorescence image.

25 Claims, 11 Drawing Sheets

(56) References Cited

U.S. PATENT DOCUMENTS

| | | |
|---|---|---|
| 2010/0322490 A1 | 12/2010 | Pan et al. |
| 2011/0007138 A1* | 1/2011 | Zhang .................... G06T 17/00 348/50 |
| 2011/0085714 A1 | 4/2011 | Yan et al. |
| 2011/0085715 A1* | 4/2011 | Yan et al. .................... 382/128 |
| 2012/0013722 A1* | 1/2012 | Wong ................ A61B 1/00009 348/66 |
| 2012/0177284 A1* | 7/2012 | Wang .................... G06T 7/0075 382/154 |

OTHER PUBLICATIONS

Commonly Assigned U.S. Appl. No. 12/965,945, entitled: Method for Identification of Dental Caries in Polychromatic Images, filed Dec 13, 2010, inventors: Jiayong Yan et al.

Supplementary European Search Report, Application No. EP12822177, May 7, 2015, 2 pages.

Richard Szeliski, Image Alignment and Stitching: A Tutorial, XP-002680820, Dec. 2006, pp. 1-87.

* cited by examiner

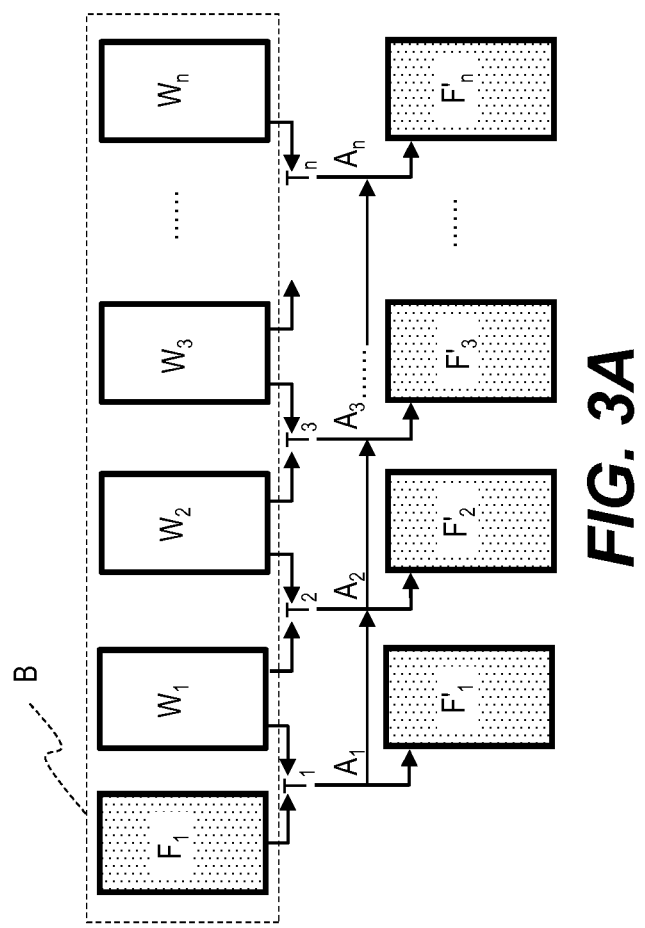

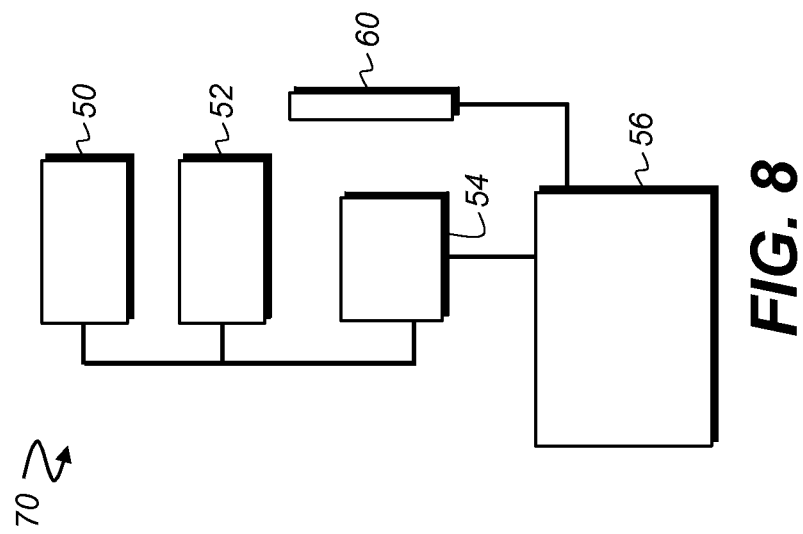

IDENTIFICATION OF DENTAL CARIES IN LIVE VIDEO IMAGES

FIELD OF THE INVENTION

The invention relates generally to the field of dental imaging, and in particular to a method and an apparatus for detection of caries. More specifically, the invention relates to a method and an apparatus for identifying and highlighting dental caries in displayed still and live video tooth images.

BACKGROUND OF THE INVENTION

While there have been improvements in detection, treatment and prevention techniques, dental caries remains a prevalent condition affecting people of all age groups. If not properly and promptly treated, caries could lead to permanent tooth damage and even to loss of teeth.

In response to the need for improved caries detection methods, various dental imaging systems, such as intraoral cameras, have been developed for early caries detection. Intraoral cameras support still mode and live mode.

PCT/CN2009/000078, entitled METHOD FOR DETECTION OF CARIES, by Wang et al., which published as WO 2010/083623, and US 2008/0056551, entitled METHOD FOR DETECTION OF CARIES, by Wong et al. describe a method that employs both reflectance and fluorescence images of the tooth to detect caries. The technique, referred to as Fluorescence Imaging with Reflectance Enhancement (FIRE), helps to increase the contrast of images over that of earlier approaches, and also makes it possible to detect incipient caries at stages when preventive measures are likely to take effect. Advantageously, FIRE detection can be more accurate at an earlier stage of caries infection than has been exhibited using existing fluorescence approaches that measure fluorescence only.

US 2010/0322490, entitled METHOD FOR QUANTIFYING CARIES, by Pan et al. and US 2011/0085714, entitled METHOD FOR EXTRACTING A CARIES LESION AREA, by Yan et al. describe methods for identification of dental caries in FIRE-based still images. Although these methods can also be applied to identifying dental caries in FIRE-based video images, these methods have limited use in identification of dental caries in FIRE-based live video images, primarily due to power consumption constraints and related operability and patient comfort concerns.

In order to capture a fluorescence image with good quality, a considerably larger electric current is needed to drive the excitation light source compared to that needed for capturing a white reflectance image. Consequently, it consumes much more power to capture a fluorescence image than to capture a white light image. For still image capture, the additional power consumption is acceptable. However, for live image capture, the high power consumption requirements can be a problem, even at a normal video frame rate of 20 to 30 Hz when using a conventional approach of capturing one white light image frame before or after one fluorescence image frame.

High power consumption for fluorescence image capture also generates considerable heat, which in turn increases the temperature at the head of the intraoral camera. Even at normal video frame rates, the head of the intraoral camera could become excessively hot and uncomfortable for the patient.

Thus there remains a need for an apparatus and a method that are capable of identifying dental caries in FIRE-based video images with reduced power consumption and less concern for power requirements and related heat generation.

SUMMARY OF THE INVENTION

An object of the present invention is to provide a method and an apparatus for identification of dental caries in live video images, particularly in live video intra-oral camera images.

Another object of the present invention is to provide a method and an apparatus with reduced power consumption and less heat generation for identification of dental caries in FIRE-based live video images.

An advantage of the method according to the present invention is that it consumes less power and can be used for identification of dental caries in FIRE-based live video images.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for generating live video images of a dental object, executed at least in part on data processing hardware, the method comprising capturing a plurality of blocks of digital images of the dental object, each block comprising a fluorescence image and one or more reflectance images; generating at least one registered fluorescence image from the fluorescence image and the one or more reflectance images; and generating a combined image using each of the one or more reflectance images and the at least one registered fluorescence image.

According to another aspect of the invention, there is provided an apparatus for generating live video images of a dental object, comprising a first light source for illuminating the dental object to generate a reflectance image; a second light source for illuminating the dental object to generate a fluorescence image; a sensor for capturing reflectance or fluorescence images; a controller for controlling the timing of illumination by the first and second light sources and image capture by the sensor, whereby a plurality of blocks of digital images of the dental object are captured, each block comprising a fluorescence image and one or more reflectance images; and a processor for generating a registered fluorescence image from the fluorescence image and each of the one or more reflectance images; and generating a combined image using each of the one or more reflectance images and the registered fluorescence image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 3A shows the working principle of the forward registration method.

FIGS. 5A-1 and 5A-2 show resized fluorescence and white light images, respectively.

FIGS. 5B-1 and 5B-2 show edge images after edge detection, of resized fluorescence and white light images, respectively.

FIGS. 5C-1 and 5C-2 show shifted edge images after preliminary motion search-based coarse registration.

FIGS. 5D-1 and 5D-2 show edge masks for shifted fluorescence edge image and shifted white light edge image, respectively.

FIGS. 5E-1 and 5E-2 show refined edge images after masking.

FIG. 8 is a schematic block diagram of an apparatus for live video imaging using combined fluorescence and white light images.

DETAILED DESCRIPTION OF THE INVENTION

Figure 1:
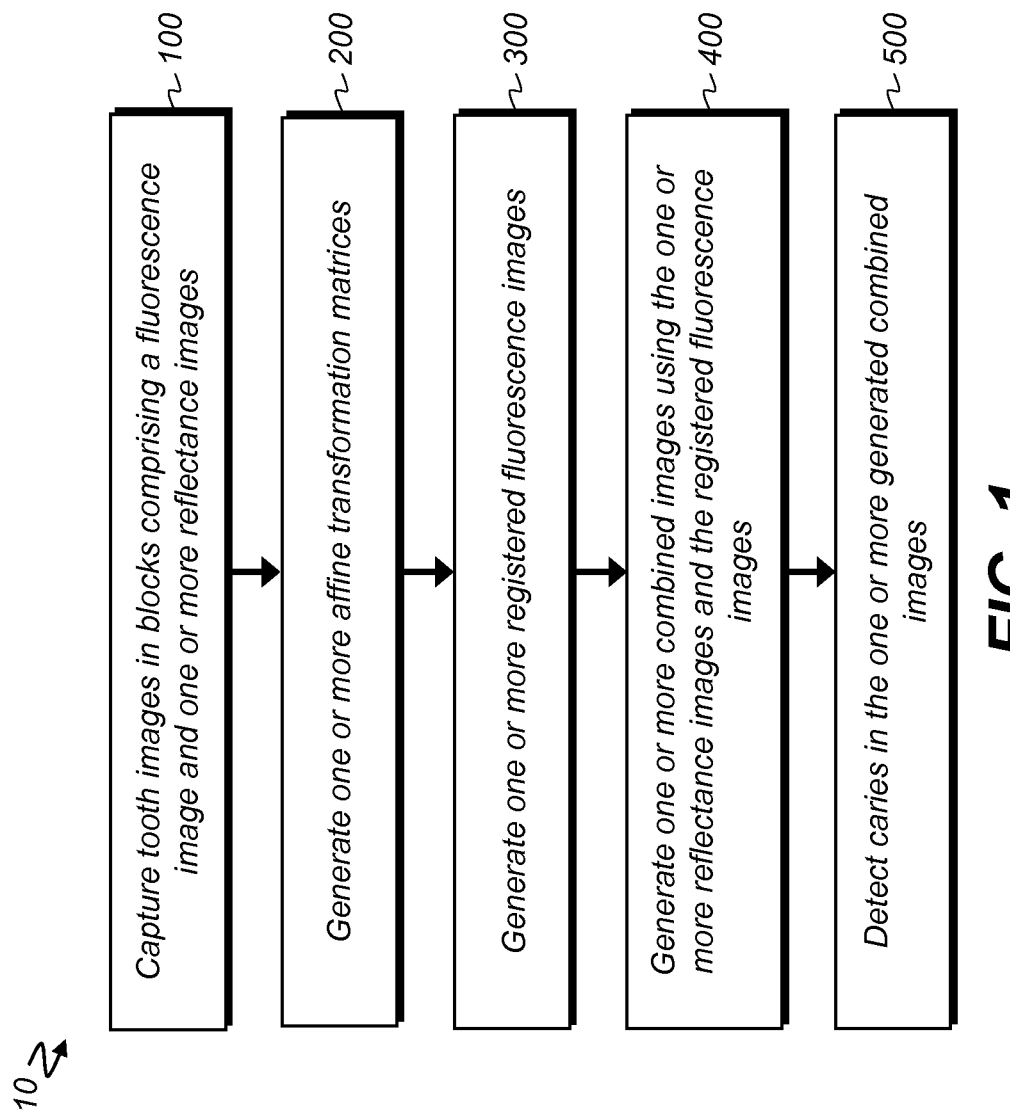
FIG. 1 shows a method for identification of caries in real-time video images comprising various steps according to the present invention.

The following is a detailed description of the preferred embodiments of the invention, reference being made to the drawings in which the same reference numerals identify the same elements of structure in each of the several figures.

This invention includes calculation steps. Those skilled in the art will recognize that these calculation steps may be performed by a computer or other type of data processing hardware that is provided with encoded instructions for image data processing. Because such image manipulation systems are well known, the present description is directed more particularly to algorithms and systems that execute the method of the present invention. Other aspects of such algorithms and systems, and data processing hardware and/or software for producing and otherwise processing the image signals may be selected from such systems, algorithms, components and elements known in the art. Given the description as set forth in the following specification, software implementation lies within the ordinary skill of those versed in the programming and image processing arts.

The stored instructions of such a software program may be stored in a computer readable storage medium, which may comprise, for example: magnetic storage media such as a magnetic disk or magnetic tape; optical storage media such as an optical disc, optical tape, or machine readable bar code; solid state electronic storage devices such as random access memory (RAM), or read only memory (ROM); or any other physical device or medium employed to store a computer program. Using such software, the present invention can be utilized on a data processing hardware apparatus, such as a computer system or personal computer, or on an embedded system that employs a dedicated data processing component, such as a digital signal processing chip.

In this disclosure, the word "intensity" is used to refer to light level, and is also broadly used to refer to the image value of a pixel in a digital image.

The word "caries", unless otherwise noted, is used to refer to either early caries or developed/advanced caries.

The concept of "live" or "real-time" operation relates to the ability to display results of image processing during the time the intra-oral images are being obtained. In live operation, the dentist or technician can view detection results on a display while the teeth are being scanned by the camera, providing on-the-spot feedback to the practitioner. In one embodiment of the present invention, live video images using combined fluorescence and white light or reflectance images are provided at or near video frame rates.

According to an embodiment of the present invention shown in FIG. 1, a method 10 for identification of caries comprises a step 100 of capturing a plurality of blocks of digital tooth images, each block of tooth images comprising a fluorescence image and one or more reflectance images; a step 200 of generating an affine transformation matrix for each of the one or more reflectance images; a step 300 of generating a registered fluorescence image from the fluorescence image and the affine transformation matrix for each of the one or more reflectance images; a step 400 of generating a combined image using each of the one or more reflectance images and the registered fluorescence image; and a step 500 of detecting caries in the generated combined images. Reflectance images can be generated with illumination of any suitable wavelength. While the subsequent sections are described in terms of a white light reflectance image or white light image, the description for generation and use of white light images are applicable to reflectance images using visible light of any suitable color.

The combined image is generated from processing and combination of fluorescence and reflectance images. While the subsequent description gives details on generating a combined image generated using the FIRE methods, the description given herein is applicable to combined images generated from processing the fluorescence and reflectance images in other ways.

Step 100 of Capturing Tooth Images in Blocks

Herein, the term "tooth image" is used to represent a frame of a video tooth image or any static tooth image or other type of dental object or feature. Generally, a digital tooth image can be classified or segmented into three groups or regions: gum, tooth region, and other background. Caries identification is only needed for a tooth as the dental object, that is, within the tooth region.

Generally, a white light image is a type of reflectance image obtained under white light or broadband or polychromatic illumination. As such, the terms "white light image" and "reflectance image" can be used interchangeably throughout this application to denote the same type of image. A fluorescence image is typically obtained under blue excitation light. Both the fluorescence and white light or reflectance images comprise actual intensity values for a region of pixels corresponding to the tooth, gum, and background objects. In general, the intensity of early caries regions in a white light image is higher than that of their surrounding sound areas. In contrast, the intensity of caries regions in a fluorescence image is lower than that of their surrounding sound areas because of fluorescence loss in caries regions.

In live video operation, according to the present invention, for each fluorescence image or between any two successive fluorescence images, one or more frames of white light or reflectance images are captured. One fluorescence image and its neighboring white light images form a block of images. The number of images in the block of images can vary depending on how the neighboring white light images are chosen relative to the fluorescence image, as will be explained further below. Note that, as used in this application, the term "neighboring" refers to adjacency in time and relates to temporal sequencing of successive images. Neighbor or neighboring images are successive images, rather than spatially adjacent images.

According to one embodiment of the present invention, referred to as the forward registration method hereinafter, each block of tooth images comprises a fluorescence image and one or more white light images that follow the fluorescence image in temporal sequence.

Figure 2A:
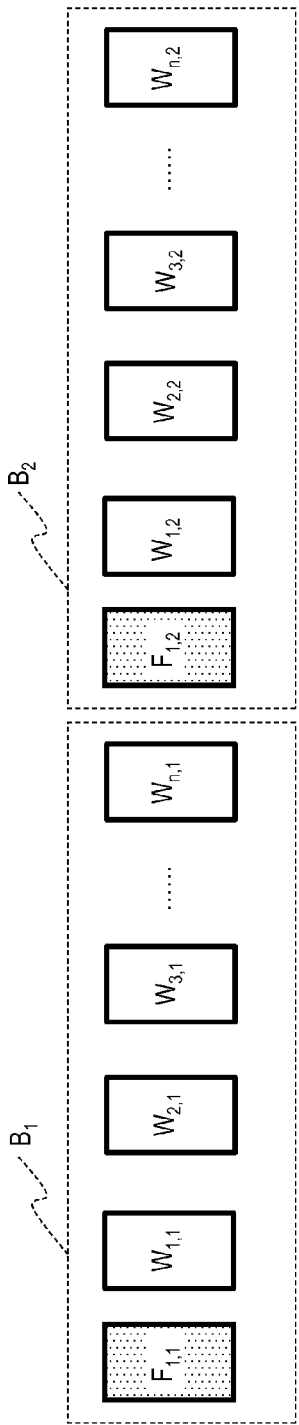
FIG. 2A shows two blocks of digital tooth images processed using a forward registration method according to the present invention.

FIG. 2A shows two blocks of tooth images $B_1$ and $B_2$. Block $B_1$ comprises a fluorescence image represented by $F_{1,1}$ and n successive frames of white light images represented by $W_{1,1}$, $W_{2,1}$, $W_{3,1}$, ..., and $W_{n,1}$. Likewise, block $B_2$ comprises a fluorescence image represented by $F_{1,2}$ and n successive frames of white light images represented by $W_{1,2}$, $W_{2,2}$, $W_{3,2}$, ..., and $W_{n,2}$. The first subscript i of $W_{i,j}$ and $F_{i,j}$ refers to the index for the i-th frame in the same block and the second subscript j refers to the index for the j-th block. In this method, the number ratio, defined as the ratio of the number of white light images in one block to the number of fluorescence images in that same block, is n.

Figure 2B:
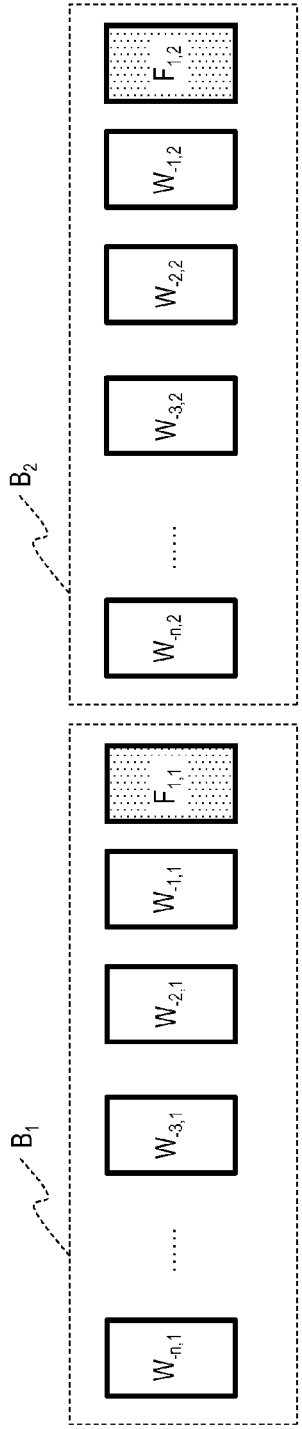
FIG. 2B shows two blocks of digital tooth images processed using a backward registration method according to the present invention.

Similarly, FIG. 2B shows two blocks of tooth images $B_1$ and $B_2$ for another embodiment of the present invention, using a method referred to hereinafter as backward registration. In this embodiment, each block of tooth images comprises a sequence of one or more successive white light images followed by a fluorescence image. In block $B_1$, n successive frames of white light images $W_{-n,1}$ ..., $W_{-3,1}$, $W_{-2,1}$, and $W_{-1,1}$ precede fluorescence image $F_{1,1}$. The number ratio is also equal to n.

Figure 2C:
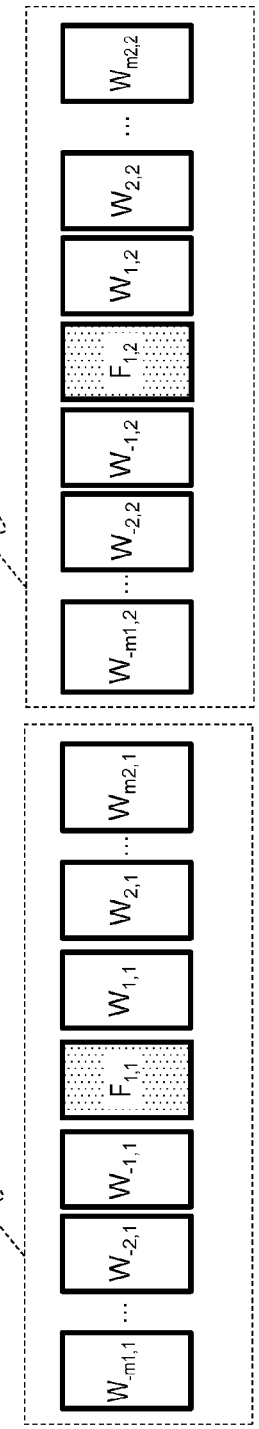
FIG. 2C shows two blocks of digital tooth images processed using a bi-directional registration method according to the present invention.

FIG. 2C shows two blocks of tooth images $B_1$ and $B_2$ for yet another embodiment of the present invention, referred to hereinafter as the bi-directional registration method. According to this embodiment, each block of tooth images comprises a sequence of one or more white light images, a fluorescence image, and then one or more additional white light images. For example, in block $B_1$, there are m1 successive frames of white light images represented by $W_{-m1,1}$, ..., $W_{-2,1}$, $W_{-1,1}$ preceding fluorescence image $F_{1,1}$ and m2 successive frames of white light images $W_{1,1}$, $W_{2,1}$, ..., and $W_{m2,1}$ following fluorescence image $F_{1,1}$. In this method, the number ratio is equal to m1+m2. It should be noted that the number m1 of white light images prior to the fluorescence image may generally be different from the number m2 of white light images after the fluorescence image, and the number ratio is the total number of white light images in one block.

In general, the higher the number ratio, the lower the power consumption, because fewer fluorescence images are captured for the same number of white light or reflectance images. However, with fewer fluorescence images motion discontinuity can be more noticeable. In practice, the inventors have found that the number ratio can be tuned to reduce power consumption, yet achieve acceptable motion continuity. It has been found that the number ratio, as defined previously, is preferably in the range between 2 and 12, and more preferably in the range between 3 and 6, for achieving the best motion continuity with acceptable power consumption. The number ratio becomes the same as the number of the white light or reflectance images when there is only one fluorescence image in each block.

It is also noted that, according to an embodiment of the present invention, the number ratio can be one. When the number ratio is one, the method according to the present invention is still different from FIRE imaging as taught in the Wong et al. '6551 publication. According to embodiments of the present invention, one or more registered fluorescence images are generated from a single captured fluorescence image, using transforms obtained from successive white light or reflectance images. These synthetic or interpolated registered fluorescence images are then combined with white light or reflectance images and used to generate a corresponding sequence of FIRE images. In contrast, in the original method taught in the Wong et al. '6551 disclosure, the captured fluorescence image is combined with a reflectance image and used to generate a FIRE image. Even though the number ratio of one may not be desirable today due to high power consumption, it is still possible that the power consumption can be reduced by other means such as using more efficient light sources, for example. The number ratio of one can be used to ensure the best motion continuity. Additionally, in the live video mode, because the camera may be moving when images are captured, it is advantageous to use the registered fluorescence image and the captured white light image to generate a FIRE image.

Step 200 of Generating One or More Affine Transformation Matrices Forward Registration FIG. 3A schematically shows how an affine transformation matrix is generated using the forward registration method. For simplicity, only one block B of tooth images is shown. In block B, just like in block $B_1$ or $B_2$ in FIG. 2A, there are, sequentially, one fluorescence image $F_1$ and n frames of white light or reflectance images $W_1$, $W_2$, $W_3$, ..., and $W_n$. The second subscript associated with different block is dropped.

First, a transformation matrix between any two neighboring image frames is generated. Specifically, transformation matrix $T_1$ is generated from fluorescence image $F_1$ and the immediately following white light image $W_1$. Transformation matrix $T_2$ is generated from white light images $W_1$ and $W_2$. Transformation matrix $T_3$ is generated from white light or reflectance images $W_2$ and $W_3$. And transformation matrix $T_n$ is generated from white light or reflectance images $W_{n-1}$ and $W_n$.

Then the affine transformation matrix for each white light or reflectance image is generated from the transformation matrices $T_1$, $T_2$, $T_3$, ..., $T_n$. Specifically, for white light image $W_1$, the affine transformation matrix $A_1 = T_1$; for white light image $W_2$, the affine transformation matrix $A_2 = T_1 T_2$; for white light image $W_3$, the affine transformation matrix $A_3 = T_1 T_2 T_3$; and for white light image $W_n$, the affine transformation matrix $A_n = T_1 T_2 T_3 \ldots T_n$.

Backward Registration

Figure 3B:
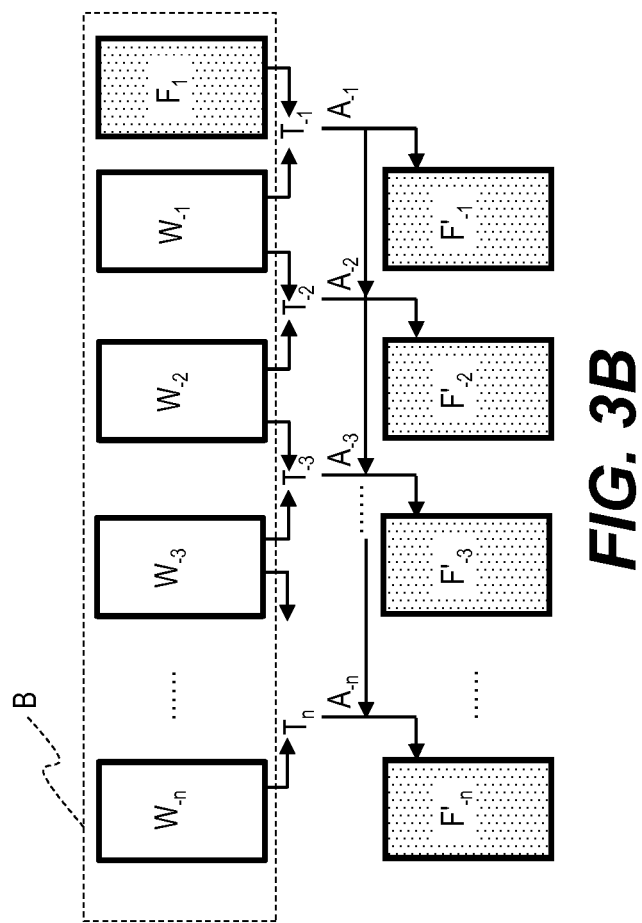
FIG. 3B shows the working principle of the backward registration method.

FIG. 3B schematically shows how an affine transformation matrix is generated using the backward registration method. Similar to FIG. 3A, only one block B of tooth images is shown. However, in FIG. 3B n frames of white light or reflectance images $W_{-n}$, ..., $W_{-3}$, $W_{-2}$, and $W_{-1}$ precede fluorescence image $F_1$, unlike in FIG. 3A.

Transformation matrix $T_{-1}$ is generated from fluorescence image $F_1$ and the immediately preceding white light or reflectance image $W_{-1}$. Transformation matrices $T_{-2}$, $T_{-3}$, $T_{-n}$ are generated from white light or reflectance images $W_{-1}$ and $W_{-2}$, $W_{-2}$ and $W_{-3}$, and $W_{-(n-1)}$ and $W_{-n}$, respectively.

The affine transformation matrix for each white light image is generated from the transformation matrices $T_{-1}$, $T_{-2}, T_{-3}, \ldots, T_{-n}$. Specifically, for white light or reflectance image $W_{-1}$, the affine transformation matrix $A_{-1}=T_{-1}$; for white light image $W_{-2}$, the affine transformation matrix $A_{-2}=T_{-2}T_{-1}$; for white light or reflectance image $W_{-3}$, the affine transformation matrix $A_{-3}=T_{-3}T_{-2}T_{-1}$; and for white light or reflectance image $W_{-n}$, the affine transformation matrix $A_{-n}=T_{-n} \ldots T_{-3}T_{-2}T_{-1}$.

Note that the order of calculating the transformation matrix between any two neighboring image frames is different between backward registration method and forward registration method.

Because the fluorescence image arrives prior to the n frames of white light or reflectance images in the forward registration method, the affine matrix for a white light image can be calculated once the white light image is available.

In comparison, the fluorescence image arrives after the n frames of white light or reflectance images in the backward registration method. As a result, the affine matrix for a white light image can be calculated only after all n frames of white light images and the fluorescence image are available.

Bi-Directional Registration

Figure 3C:
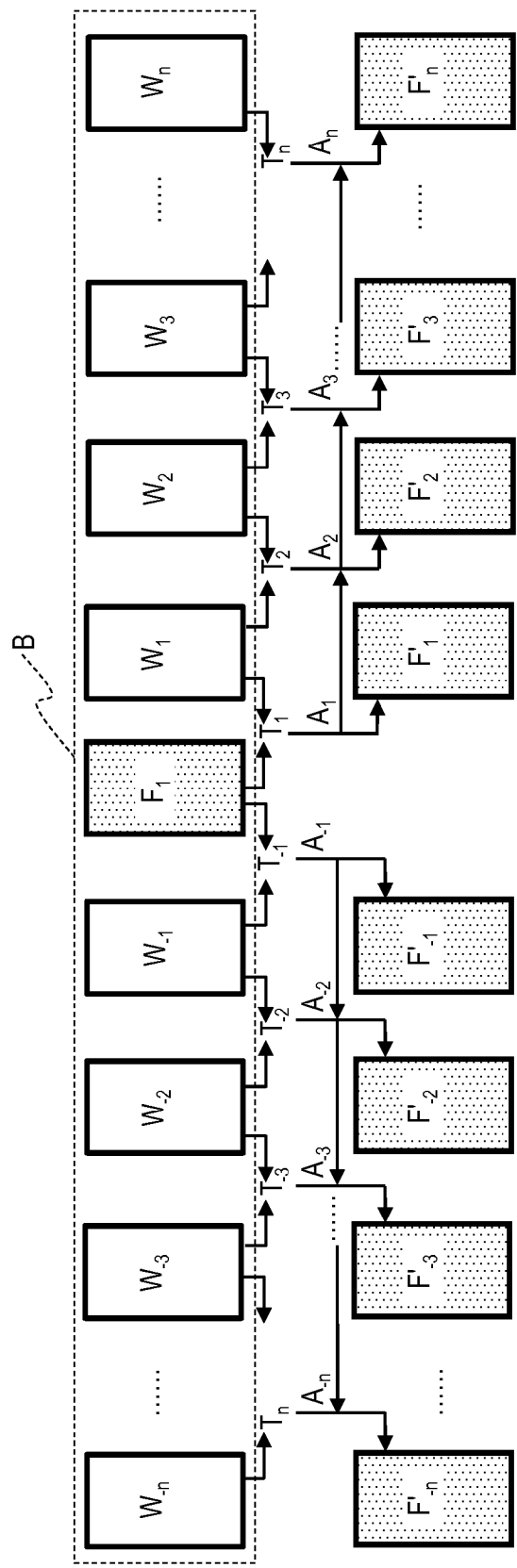
FIG. 3C shows the working principle of the bi-directional registration method.

FIG. 3C schematically shows how an affine transformation matrix is generated using the bi-directional registration method. This method essentially combines the forward and backward registration methods. In this method, one block B of tooth images still has only one fluorescence image $F_1$. However, there are n frames of white light or reflectance images $W_{-n}, \ldots, W_{-3}, W_{-2}$, and $W_{-1}$ prior to fluorescence image $F_1$, and n frames of white light or reflectance images $W_1, W_2, W_3, \ldots$, and $W_n$ after fluorescence image $F_1$. Note that for convenience, in FIG. 3C the numbers m1 and m2 of white light images prior to and after the fluorescence image are both considered to be equal to n.

Using the same procedure as described referring to the forward registration method, transformation matrices $T_1, T_2, T_3, \ldots, T_n$ and affine transformation matrices $A_1, A_2, A_3, \ldots, A_n$ are calculated for each of white light or reflectance images $W_1, W_2, W_3, \ldots$, and $W_n$ following fluorescence image $F_1$.

Using the same procedure as described referring to the backward registration method, transformation matrices $T_{-1}$, $T_{-2}, T_{-3}, \ldots, T_{-n}$ and affine transformation matrices $A_{-1}$, $A_{-2}, A_{-3}, \ldots, A_{-n}$ are calculated for each of white light or reflectance images $W_{-1}, W_{-2}, W_{-3}, \ldots$, and $W_{-n}$ preceding fluorescence image $F_1$.

For the same motion continuity, roughly measured by the time interval between the fluorescence image $F_1$ and the farthest white light image $W_n$ or $W_{-n}$ for all three methods, the number ratio in the bi-directional registration method is twice those in the forward and backward registration methods. Thus, the bi-directional registration method consumes less power.

There is no delay in generating the registered fluorescence images in the forward registration method, while there is an undesired delay in generating the registered fluorescence images for those white light images prior to the fluorescence image in the backward registration method and the bi-directional registration method. However, for the same number ratio, the motion between the first white light image and the last white light image in one block in the forward registration method is unfavorably larger than that in the bi-directional registration method. Thus the bi-directional registration method achieves a trade-off between the acceptable delay and motion continuity.

Sub-Steps of Generating Transformation Matrix $T_i$

In the following, the calculation of transformation matrix $T_i$, where i=1, . . . , n for FIG. 3A, i=−1, . . . , −n for FIG. 3B, and i=±1, . . . , ±n for FIG. 3C, respectively, is described in detail referring to FIG. 4 through FIG. 5E-2.

Figure 4:
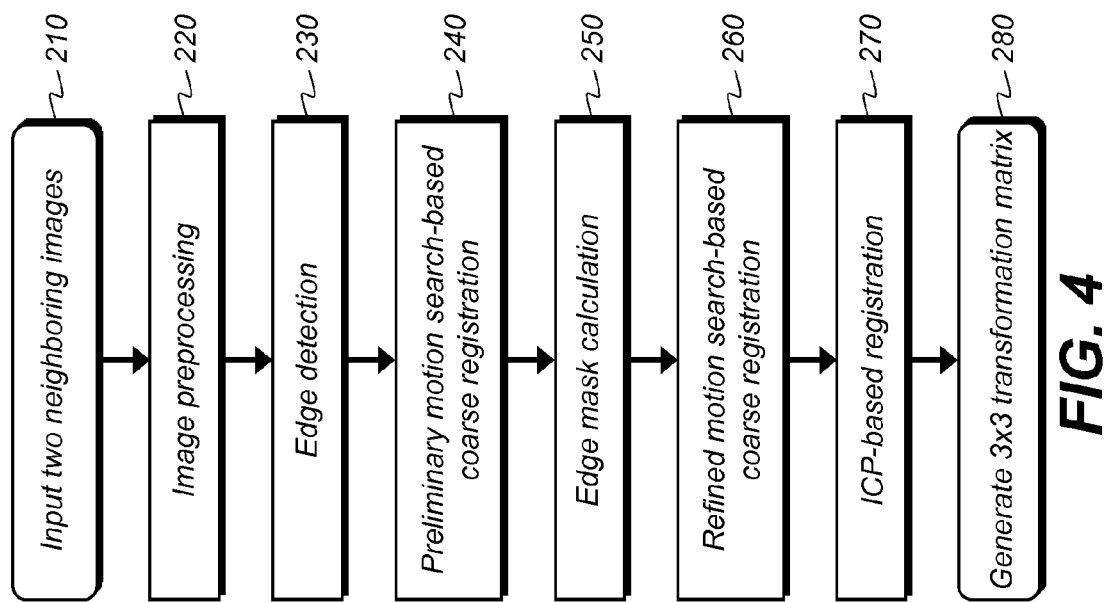
FIG. 4 shows a flowchart for generating a transformation matrix including various sub-steps.

Referring to FIG. 4, generating a transformation matrix for any two neighboring images comprises the steps of generating two resized images from the two neighboring images; generating two tooth edge images from the two resized images; generating two shifted edge images by calculating the translations in x and y directions between the two edge images; generating two refined edge images from the two shifted edge images by using a tooth edge mask; generating two modified edge images from the two refined edge images; and producing the transformation matrix by using an iterative closest point-based registration algorithm and the two modified edge images. This process will be described below with reference to FIG. 4, referring to the following sub-steps following an image input step 210: image preprocessing step 220; edge detection step 230; preliminary motion search-based coarse registration 240; edge mask calculation 250; refined motion search-based coarse registration 260; and iterative closest point (ICP)-based registration 270; with generation of the 3×3 matrix 280.

Two neighboring images can be a fluorescence image and a white light image, or can be two white light images. The sub-steps of generating a transformation matrix for a fluorescence image and a white light image are the same as for two white light images. For simplicity, in the following description referring to FIG. 4 and FIG. 5, two neighboring images are taken as a fluorescence image and a white light or reflectance image.

Image Preprocessing

According to the present invention, the image preprocessing sub-step aims to reduce the size of input fluorescence image $F_1$ and white light or reflectance image $W_1$ and subsequently produce resized fluorescence and white light images that have a proper size. The processing time using resized fluorescence and white light images at later sub-steps is shortened, yet the resolution of the resized images is only slightly affected and is still acceptable. In one example, the width and the height of the resized images are ⅓ of the respective width and height of the input images. In another example, the resized images have the same width and height as the input images. Namely, the resized images are the same as input images. The width of resized images is desired to be a multiple of 8.

Figures 2, 5A:
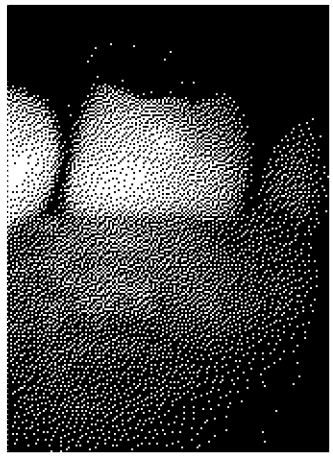

FIG. 5A-1 and FIG. 5A-2 show resized fluorescence image and white light image, respectively.

Edge Detection

Figures 2, 5B:
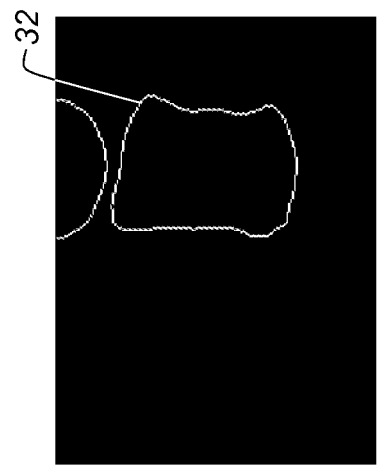
Figures 1, 5A:
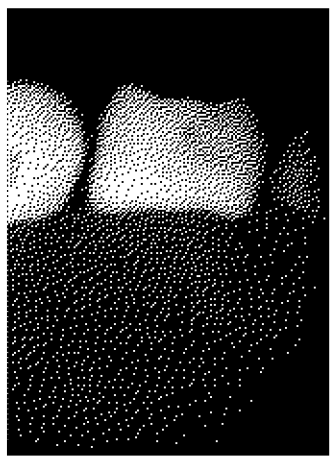
Figures 1, 5B:

According to the present invention, feature points are used in the registration methods (forward, backward, and bi-directional). In one embodiment, the feature points are edge points corresponding to boundaries between tooth and gum/background in the resized fluorescence image and resized white light image. Various detectors can be used to detect edge points. In one example, a Canny edge detector is used to detect edge points. The Canny edge detector is a widely used algorithm for edge detection. The resultant edge is one pixel in width. FIGS. 5B-1 and 5B-2 show a fluorescence edge image and a white light edge image, respectively. The edge images include not only tooth boundaries 32 between tooth and gum, but also undesired points 30 such as strong edges in other parts of the images.

Canny edge detection is familiar to those skilled in the art. Generally, it comprises four stages: noise reduction, finding the intensity gradient of the image, non-maximum suppression, and hysteresis thresholding. In one example, a 5×5 Gaussian filter is applied for noise reduction and a 5×5 Sobel operator is used to calculate the intensity gradient of the image. The Canny algorithm contains a number of adjustable parameters, such as low threshold and high threshold in the hysteresis thresholding step. The parameters are selected based on experiments. Typically, the numbers of the edge points in the two edge images are selected to be the same, and the edge points are equally spaced.

Preliminary Motion Search-Based Coarse Registration

When fast motion exists between two sequential frames, edge images obtained from the previous edge detection step may not be accurate enough to obtain the transformation matrix because the iterative closest point (ICP)-based registration algorithm used in the following sub-step converges only if two edge images are close to each other. According to an embodiment of the present invention, a preliminary motion search-based coarse registration is used to improve the accuracy of obtaining the transformation matrix.

First, the distance between two edge images I1 and I2 is calculated as the sum of distance of each point in edge image I1 to edge image I2 and distance of each point in edge image I2 to edge image I1. Generally, the distance of one point to an edge image is the least distance between the point and each point in the edge image.

Second, the search range is determined by the distance of two edge images. In one example, the search range is set to two times the mean distance, where the mean distance is equal to the distance of two edge images divided by the total number of points in each of the two images.

Third, full search for best match is performed by calculating the match criteria for each point in the search range. The criterion for best match is the distance between two edge images. When the difference between current distance and previous distance is smaller than a preset threshold or the iteration process reaches a preset maximum iteration number, the iteration process terminates.

Alternatively, smart search methods searching for partial points in the search range can also be used.

Figures 2, 5C:

After this step, translations in x and y directions between two edge images are obtained. FIG. 5C-1 and FIG. 5C-2 are results of the preliminary motion search-based coarse registration. Compared to the edge images in FIGS. 5B-1 and 5B-2, the shifted edge images in FIGS. 5C-1 and 5C-2 have been shifted downward, reflecting translations in x and y directions.

Edge Mask Calculation

Figures 2, 5D:
Figures 1, 5C:
Figures 1, 5D:

In the edge images shown in FIGS. 5B-1 and 5C-1, some undesired points 30 may appear and affect the registration accuracy. Undesired points 30 are not part of the tooth edge. To remove undesired points 30, edge mask images shown in FIGS. 5D-1 and 5D-2 are used. Edge masks, represented by white points shown in the edge mask images, contain the possible edge pixel locations. Edge masks shown in FIGS. 5D-1 and 5D-2 are the same for the fluorescence image and white light image. The points that are not located in the masks are removed.

The edge masks are the edge of tooth areas according to mathematical morphology. The tooth areas are obtained using a threshold method. In the white light images, the ratio between green channel and red channel is further employed to get accurate tooth areas. The final tooth area is determined by binary image reconstruction using two tooth areas of the resized fluorescence image and white light image shown in FIG. 5A-1 and FIG. 5A-2, respectively.

Figures 2, 5E:
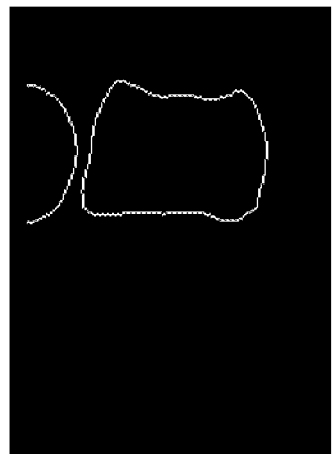

FIGS. 5E-1 and 5E-2 show refined edge images after masking the edge images in FIGS. 5C-1 and 5C-2 using the edge masks shown in FIGS. 5D-1 and 5D-2, respectively.

Refined Motion Search-Based Coarse Registration

Refined motion search-based coarse registration is similar to the preliminary motion search-based coarse registration described above. They both have the same search criteria. They both are performed through full search in the same search range. However, refined motion search-based coarse registration is performed over the refined edge images after undesired points have been removed. Consequently, the obtained translations in x and y directions between two refined edge images are more accurate than those from the preliminary motion search-based coarse registration.

The more accurate translations in x and y directions are then used to modify two refined edge images to produce two modified edge images.

Iterative Closest Point (ICP)-Based Registration

ICP is an algorithm employed to minimize difference between two clouds of points. According to embodiments of the present invention, ICP is used to register the two modified edge images. The output of ICP-based registration algorithm is a 3×3 rotation matrix. This rotation matrix is the transformation matrix $T_i$, where i=1, ..., n for FIG. 3A, i=−1, ..., −n for FIG. 3B, and i=±1, ..., ±n for FIG. 3C, respectively.

The motion between two neighboring images is assumed to be represented by the affine transformation matrix $A_i$ shown in FIGS. 3A-3C. An affine transformation is a combination of linear transformations (rotation, scaling, or shear) and a translation (or "shift") transformation. The affine transformation is also represented by a 3×3 matrix.

Then the affine transformation matrix for each white light or reflectance image is generated from the transformation matrix $T_i$ as described above referring to FIGS. 3A-3C.

Step 300 of Generating One or More Registered Fluorescence Images

Because in each block there is only one fluorescence image captured for n frames of white light images, there is a need to generate n frames of interpolated or synthetic fluorescence images, each of which is registered with the corresponding white light image.

The i-th registered fluorescence image $F'_i$ shown in FIGS. 3A-3C is generated through a process called image warping to register with the i-th white light image $W_i$, where i=1, ..., n for FIG. 3A, i=−1, ..., −n for FIG. 3B, and ±n for FIG. 3C, respectively.

The fluorescence image $F_1$ and the affine transformation matrix $A_i$ are inputs to image warping, familiar to those skilled in the art. The affine transformation matrix $A_i$ describes the relationship between the coordinates in the white light image $W_i$ and the coordinates in the fluorescence image $F_1$. It controls how to transform the fluorescence image $F_1$ to produce the registered fluorescence image $F'_i$. The coordinates of pixels in the registered fluorescence image $F'_i$ are projected onto input fluorescence image $F_1$ by the affine transformation matrix $A_i$ to calculate the value of the pixels in the registered fluorescence image $F'_i$. And the value of the pixels in the registered fluorescence image $F'_i$ is calculated, for example, by bilinear interpolation of pixel values in input fluorescence image $F_1$.

Figure 6B:
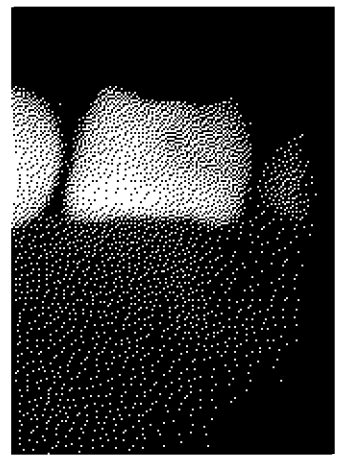
FIG. 6B shows a registered fluorescence image.
Figures 1, 5E:
Figure 6A:
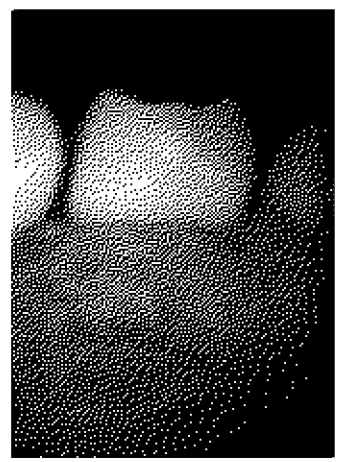
FIG. 6A shows a white light image.

FIG. 6A shows white light image $W_i$, and FIG. 6B shows the registered fluorescence image $F'_i$ that has been registered with the white light image, where i=1, . . . , n for FIG. 3A, i=−1, . . . , −n for FIG. 3B, and i=±1, . . . , ±n for FIG. 3C, respectively.

Step 400 of Generating One or More Combined Images

The registered fluorescence image $F'_i$ and the white light image $W_i$ form a pair of fluorescence and white reflectance images, where i=1, . . . , n for FIG. 3A, i=−1, . . . , −n for FIG. 3B, and ±n for FIG. 3C, respectively. This pair of fluorescence and white reflectance images can then be used to generate a combined image such as a FIRE image using previously disclosed methods.

In one example, the FIRE image is generated according to a downshifting method, as disclosed in commonly-assigned U.S. Pat. No. 7,668,355, entitled METHOD FOR DETECTION OF CARIES, by Wong et al.

In another example, the FIRE image is generated according to a morphological method, as disclosed in commonly-assigned PCT/CN2009/000078, entitled METHOD FOR DETECTION OF CARIES. The FIRE image is obtained through subtracting regional maxima and dome regions of the reflectance image from the fluorescence image. As a result, the FIRE image has a similar appearance to a fluorescence image because both have lower intensity values in a lesion area than in a surrounding sound area. However, the FIRE image has higher contrast than a fluorescence image, making it potentially more sensitive in detecting caries. The FIRE image generated using this method has reduced sensitivity to illumination variation.

After this step, one or more combined images are generated. This results in a stream of combined image frames at the same frame rate as the white light image frames. The frame rate can be at or near normal video rates.

Step 500 of Detecting Caries in the One or More Combined Images

Detection of dental caries in the one or more combined images such as FIRE images is then performed according to the methods described in commonly-assigned copending U.S. Patent Application Publication Nos. 2010/0322490, entitled METHOD FOR QUANTIFYING CARIES, and 2011/0085714, entitled METHOD FOR EXTRACTING A CARIES LESION AREA. The detection results can be displayed as highlights on the video stream of reflectance images $W_i$ or registered fluorescence images $F'_i$, in a similar manner as disclosed in commonly-assigned copending U.S. Patent Publication No. 2009/0185712, entitled METHOD FOR REAL-TIME VISUALIZATION OF CARIES CONDITION and U.S. patent application Ser. No. 12/965,945, entitled METHOD FOR IDENTIFICATION OF DENTAL CARIES IN POLYCHROMATIC IMAGES.

In an alternate embodiment, the FIRE images may be directly displayed as live video for viewing. In this case, the FIRE image frames may be displayed with or without detection results being highlighted.

While the specification is described in terms of teeth imaging, the invention is applicable to imaging of any dental objects, including but not limited to teeth, gum, tongue, throat, tonsil, palate, and oral mucosa.

Figure 7:
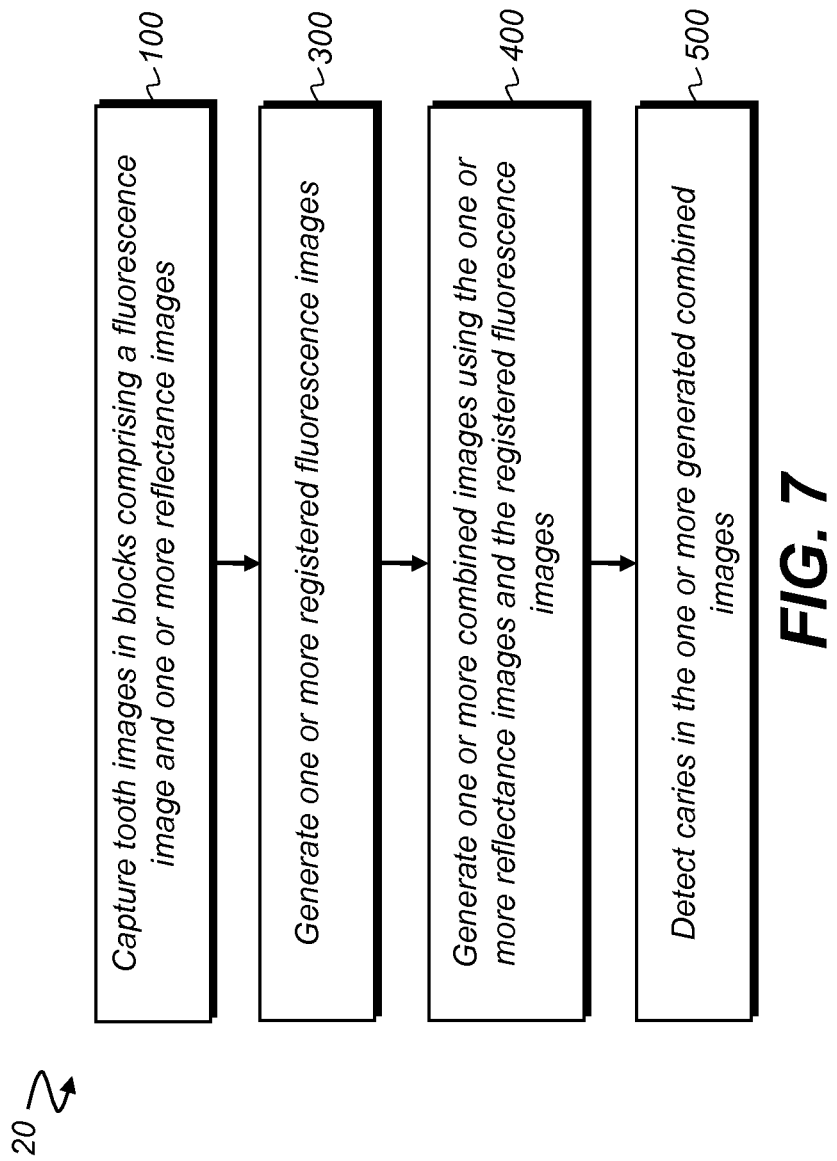
FIG. 7 is a logic flow diagram showing a method for identification of caries in real-time video images in an alternate embodiment of the present invention.

While the method 10 for identification of caries referring to FIG. 1 comprises step 100 of capturing tooth images in blocks, step 200 of generating one or more affine transformation matrices, step 300 of generating one or more registered fluorescence images, step 400 of generating one or more combined images, and step 500 of detecting caries in the one or more generated combined images, method 10 can be modified as shown in FIG. 7 to provide a method 20 for generating live video images of a dental object. Method 20 comprises step 100 of capturing tooth images in blocks, step 300 of generating one or more registered fluorescence images, and step 400 of generating one or more combined images with caries detection following in step 500. In method 20, step 300 further comprises generating an affine transformation matrix for each of the one or more reflectance images, wherein the affine transformation is subsequently used to generate the registered fluorescence image. Alternatively, techniques other than the affine transformation matrix can be used to generate the one or more registered fluorescence images. Optionally, method 20 may further comprise displaying the one or more combined images as live video, or comprise detecting caries in the generated combined images, and then displaying the detected caries as highlights on the video stream of the one or more reflectance images, registered fluorescence images, or combined images.

Apparatus for Generating Live Video Images of a Dental Object

The above method 10 of FIG. 1 or 20 of FIG. 7 can be implemented in an apparatus for generating live video images of a dental object. The schematic diagram of FIG. 8 shows an imaging apparatus 70 comprises a first light source 50 such as a white light source for illuminating the dental object to generate one or more reflectance images and a second light source 52 for illuminating the dental object to generate a fluorescence image. The second light source 52 can be a UV or blue light emitting diodes (LEDs) or other source that emits light for exciting fluorescent emission. For example, its spectral range may be within 300-500 nm.

The apparatus 70 also comprises a sensor 60 for capturing reflectance or fluorescence images and a controller 54 for controlling the timing of illumination by the first and second light sources 50 and 52 and image capture by sensor 60. Sensor 60 captures a plurality of blocks of digital images of the dental object, wherein each block comprises the fluorescence image and the one or more reflectance images. Sensor 60 can be a CMOS or CCD device, for example.

The apparatus further comprises a processor 56 for generating a registered fluorescence image from the fluorescence image and each of the one or more reflectance images; and generating a combined image using each of the one or more reflectance images and the registered fluorescence image. Generating the registered fluorescence image optionally further comprises generating an affine transformation matrix for each of the one or more reflectance images, wherein the affine transformation is subsequently used to generate the registered fluorescence image.

The apparatus further optionally comprises a display for displaying the generated combined image as live video.

The processor further optionally performs caries detection on the generated combined image. The caries detection results can be displayed as highlights on live video of the generated combined image, the one or more registered fluorescence images, or the one or more captured reflectance images.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST 10 method for identification of caries
20 method for generating live video images of a dental object
30 undesired points
32 tooth boundaries
50, 52 light source
54 controller
56 processor
60 sensor
70 imaging apparatus
100 step of capturing tooth images in blocks
200 step of generating one or more affine transformation matrices
210 image input step
220 image preprocessing step
230 edge detection step
240 coarse registration
250 edge mask calculation
260 coarse registration
270 iterative closest point (ICP)-based registration
280 generation of the 3×3 matrix
300 step of generating one or more registered fluorescence images
400 step of generating one or more combined images
500 step of detecting caries in the one or more generated combined images

What is claimed is:

1. A method for generating live video images of a dental object, executed at least in part on data processing hardware, the method comprising:
   obtaining real-time video images of a dental object;
   dividing the real-time video images of the dental object into a plurality of blocks of temporal sequenced successive digital images of the dental object, at least one block comprising a fluorescence image and more than one sequenced reflectance images;
   generating at least one registered fluorescence image from the fluorescence image and one or more reflectance images; and
   generating a combined image using each of the one or more reflectance images and the at least one registered fluorescence image.

2. The method of claim 1, wherein generating the at least one registered fluorescence image further comprises generating an affine transformation matrix for each of the more than one temporally sequenced reflectance images, wherein the affine transformation is subsequently used to generate the at least one registered fluorescence image.

3. The method of claim 2, wherein generating the affine transformation matrix comprises generating a transformation matrix between any two neighboring images.

4. The method of claim 3, wherein generating the transformation matrix comprises generating two edge images from the two neighboring images and utilizing an iterative closest point-based registration algorithm.

5. The method of claim 4 further comprising generating a tooth edge mask according to a ratio between green channel and red channel in one of the two neighboring images.

6. The method of claim 4, wherein the two edge images are generated using Canny edge detector.

7. The method of claim 4 further comprising generating two shifted edge images using a motion search-based coarse registration method.

8. The method of claim 4 further comprising generating two modified edge images using a motion search-based coarse registration method.

9. The method of claim 1 further comprising displaying the generated combined images as live video.

10. The method of claim 1 further comprising detecting caries in the generated combined image.

11. The method of claim 10 further comprising displaying the detected caries as highlights on live video of the generated combined image, the at least one registered fluorescence image, or the one or more reflectance images.

12. The method of claim 1, wherein the number of the more than one temporally sequenced reflectance images is between 3 and 6.

13. The method of claim 1, wherein generating the at least one registered fluorescence image is performed through image warping process.

14. The method of claim 1 wherein at least one of the one or more reflectance images is a white light image.

15. The method of claim 1, wherein the one or more reflectance images precede the fluorescence image.

16. The method of claim 1, wherein the one or more reflectance images follow the fluorescence image.

17. The method of claim 16, wherein additional one or more reflectance images precede the fluorescence image.

18. An apparatus for generating live video images of a dental object, comprising:
   a first light source for illuminating the dental object to generate more than one reflectance images of a dental object;
   a second light source for illuminating the dental object to generate a fluorescence image of the dental object;
   a sensor for capturing the more than one reflectance images or the fluorescence image of the dental object;
   a controller for controlling the timing of illumination by the first and second light sources and live video images capture by the sensor, whereby a plurality of blocks of digital images of the dental object are captured, each block comprising temporal sequenced successive digital images being the fluorescence image and the more than one sequenced reflectance images of the dental object; and
   a processor for generating at least one registered fluorescence image from the fluorescence image and at least one sequenced reflectance images; and
   generating a first combined image using one reflectance image and the fluorescence image and generating second combined images using the at least one sequenced reflectance images and the at least one registered fluorescence image;
   displaying combined images as live video of the dental object.

19. The apparatus of claim 18 further comprising a display for displaying the generated combined images as live video.

20. The apparatus of claim 18, wherein the processor performs caries detection on the generated combined images.

21. The apparatus of claim 20 further comprising a display for displaying the caries detection results as highlights on live video of the generated combined images, the at least one registered fluorescence image, or the one or more reflectance images.

22. The apparatus of claim 18, wherein generating the registered fluorescence image further comprises generating an affine transformation matrix for each of the one or more reflectance images, wherein the affine transformation is subsequently used to generate the at least one registered fluorescence image.

23. A method for generating a live video image of a dental object, comprising:
   capturing a block of digital images of the dental object comprising a plurality of M temporally sequenced fluorescence images and a plurality of N temporally sequenced reflectance images, where N and M are positive integers, and where the integer N is greater than the integer M;

generating at least one registered fluorescence image for each of the N-M temporally sequenced reflectance images from one of the M temporally sequenced fluorescence images and more than one of the N-M temporally sequenced reflectance images;

generating combined images using the more than one of the plurality of reflectance images, and one of each of the plurality of fluorescence images or the at least one registered fluorescence image; and displaying the combined images as live video of the dental object.

24. The method of claim 23, wherein the number of the plurality of reflectance images is between 3 and 6.

25. The method of claim 23, wherein generating the at least one registered fluorescence image further comprises generating an affine transformation matrix for each of the plurality of reflectance images, wherein the affine transformation is subsequently used to generate the at least one registered fluorescence image.

* * * * *